| United States Patent [19] | [11] Patent Number: 4,732,996 |
| Moorhead et al. | [45] Date of Patent: Mar. 22, 1988 |

[54] TREATMENT OF ALKOXYSILANES

[75] Inventors: Kenneth W. Moorhead; Kirsten L. Reading; David J. Rengering, all of Midland; Antony P. Wright, Mills Township, Midland County, all of Mich.

[73] Assignee: Dow Corning Corporation, Midland, Mich.

[21] Appl. No.: 13,742

[22] Filed: Feb. 10, 1987

[51] Int. Cl.$^4$ ............................ C07F 7/08; C07F 7/18
[52] U.S. Cl. ..................................................... 556/466
[58] Field of Search ......................................... 556/466

[56] References Cited

U.S. PATENT DOCUMENTS 1,944,274  1/1934  Salzberg ......................... 556/466 X
2,114,866  4/1938  Vaughn ............................. 556/466

FOREIGN PATENT DOCUMENTS 11115052  5/1968  United Kingdom ........... 556/466 X

Primary Examiner—Paul F. Shaver
Attorney, Agent, or Firm—Carl A. Yorimoto

[57] ABSTRACT

A process in which the residual chloride impurities in crude alkoxysilanes with atmospheric boiling points below 130° C. are reduced in order to render the resultant alkoxysilanes more suitable as a starting intermediate for the preparation of other chemical compounds and for use in electronics applications is described. The essence of the process is contacting the alkoxysilane with an alkaline metal compound using superatmospheric pressure to achieve a treatment temperature of greater than 130° C.

21 Claims, No Drawings

TREATMENT OF ALKOXYSILANES

BACKGROUND OF THE INVENTION

This invention relates to a process in which the residual chloride impurities in crude alkoxysilanes are reduced in order to render the resultant alkoxysilane more suitable as a starting intermediate for the preparation of other chemical compounds and for use in electronics applications.

Alkoxysilanes are produced commercially via the reaction of chlorosilanes or organochlorosilanes with alcohols. One of the quality requirements for the subsequent use of alkoxysilanes as chemical intermediates in the preparation of other chemical compounds and for use in the electronics industry is the need for 5 low residual chloride content—i.e., levels down to 100 parts per million (ppm) chloride or lower on a weight basis.

Several process routes to alkoxysilanes are known in the art. Examples of known routes to alkoxysilanes are disclosed by Nitzsche et al., in U.S. Pat. No. 3,792,071, issued Feb. 12, 1974; Kotzsch et al., in U.S. Pat. No. 4,039,567, issued Aug. 2, 1977; Kotzsch et al., in U.S. Pat. No. 4,228,092, issued Oct. 14, 1980; and Schinabeck et al., in U.S. Pat. No. 4,298,753, issued Nov. 3, 1981. Another example of a process to produce alkoxysilanes from chlorosilanes and alcohols is a continuous process which comprises: (a) a distillation-column type reactor in which liquid reactants, intermediates, and product flow in a downward direction and in which vapor reactants, intermediates, and by-produced hydrogen chloride gas pass upward in countercurrent flow with liquids; (b) chlorosilane or organochlorosilane and a portion of the alcohol reactant are fed to the top of the column as liquid feeds; (c) the remainder of the alcohol reactant is fed in the lower portion of the reactor as vapor; (d) the product alkoxysilane is drawn off the bottom of the reactor as a liquid; (e) gaseous hydrogen chloride and vapors of reactants and intermediates pass out of the reactor to a means for contacting the gases and vapors with liquid methyl chloride, the methyl chloride vaporizing, cooling, and condensing vapors of reactants and intermediates, separating the gaseous hydrogen chloride as a gas with methyl chloride from the condensed reactants and intermediates; (f) passing the combined hydrogen chloride and methyl chloride stream to a means for separating and recovering the by-produced hydrogen chloride; and (g) returning the cooled liquid stream of reactants and intermediates to the reactor at a point below the entry of the feed. As a result of this configuration, the upper portion of the reactor is maintained at a temperature well below the boiling point of either of the reactants.

While the processes discussed, supra, are designed to essentially react all chlorosilane materials to alkoxysilanes, residual chloride materials remain—i.e., 500–1000 ppm chloride on a weight basis relative to the alkoxysilane produced. The residual chloride may be unreacted chlorosilanes or organic chloride material. The source of these organic chlorides may be alkyl chlorides from the direct process reaction to produce organochlorosilanes or the reaction of hydrogen chloride with olefinic materials that are impurities in the organochlorosilanes. Whatever the source of the chloride impurity, many applications of the alkoxysilanes, such as use as a chemical intermediate and for use in electronics applications, require that the residual chloride content be as low as possible.

As an example of the need for a very low chloride content, certain electronics applications require that the alkoxysilane materials have electroconductivity of approximately 5–10 micromho/centimeter (micromho/cm.). The correlation between electroconductivity value and residual chloride content is not entirely clear; however, electroconductivity goes down as chloride content goes down.

A further example of the need for very low chloride content is the use of alkoxysilanes as chemical intermediates. A specific example of the use of alkoxysilanes as chemical intermediates is the preparation of a chemical material that is prone to be highly colored. The ultimate use of this chemical material dictates the need for low color. It has been found that chloride content of the alkoxysilanes has a significant impact upon the final color of this chemical material. This relationship will be illustrated in the examples, infra.

Burzynski and Martin in Great Britain No. 1,115,052, published May 22, 1968, disclose a process in which impure alkoxysilanes are purified to "an essentially zero acid content" by distillation of the desired alkoxysilane from a mixture of the crude alkoxysilane and a reagent that converts acidic or potentially acidic species to non-acidic, non-volatile compounds. Burzynski and Martin report chloride levels of treated alkoxysilanes as low as 1 ppm. The claims of Burzynski and Martin are silent on whether or not distillation is carried out at atmospheric pressure. However, all the examples disclosed are at atmospheric pressure. Specific materials purified by this technique included methyltrimethoxysilane, with an atmospheric pressure boiling point of approximately 100° C. The reagents disclosed by Burzynski and Martin are such materials as $LiAlH_4$, sodium methoxide, aqueous sodium carbonate, aqueous sodium hydroxide, and alkali metal salts of weak organic acids. The analytical test disclosed by Burzynski and Martin consisted of the titration of residual chlorosilane material and reagent alcohol with potassium hydroxide. The inventors of the instant invention submit that Burzynski and Martin were only able to analyze for unreacted chlorosilane materials and did not detect organic chloride materials using such a method. The inventors of the instant invention further submit that Burzynski and Martin neither recognized the presence of organic chloride nor reduced the organic chloride content of methyltrimethoxysilane or alkoxysilanes with an atmospheric boiling point of less than approximately 130° C. as does the instant invention. In Example 12 of Burzynski and Martin methyltriethoxysilane with a chloride content, determined by the technique supra, of 20 ppm was distilled in the absence of any treating agent. The result was a distillate that analyzed by their analytical technique to contain approximately 150 ppm chloride. The inventors of the instant invention submit that in Example 12 of Burzynski and Martin organic chloride was present in the methyltriethoxysilane sample but was not detected by their analytical test. Upon heating, the organic chloride decomposed to form hydrogen chloride which then could be detected by their test. The conclusion one must draw is that Burzynski and Martin were not aware of the presence of chloride impurities other than ionic or hydrolyzable chloride materials. Burzynski and Martin disclose and claim a process for the removal of ionic chloride from alkoxysilanes with boiling points below approximately 130° C. There is no teaching regarding the removal of residual chlorides, as taught by the instant invention.

Asano et al., in Japanese Patent Publication OPI No. 47931/75, published Apr. 28, 1975, discloses the purification of triethoxysilane by means of reflux and distillation and the use of an inert gas purge. The principal impurities of concern are unreacted ethanol, other ethoxysilanes, hydrocarbons, ethyl ether, and ethyl chloride. Ethyl chloride is the only organic chloride specifically mentioned. This method claims the reduction of impurities to levels lower than those attained with conventional distillation. However, one drawback to this method that is apparent to the inventors is the potential loss of usable product with the inert gas. Many of the noted impurities have boiling points close to that of the product triethoxysilane. As such, one expects that the inert gas bubbled through the crude triethoxysilane carries a significant amount of the product triethoxysilane from the distillation vessel. No mention is made of this potential problem, means to recover triethoxysilane from this gas stream, or for that matter, the overall recovery efficiency of triethoxysilane.

Bezlyudnyi et al., in Soviet Union No. 852,874, issued Aug. 7, 1981, disclose the purification of alkoxysilane compounds by treatment with calcium hypochlorite at temperatures of 100°–140° C. Bezlyudnyi et al., intends to oxidize crotonic aldehydes which appear to impart color to alkoxysilanes. No mention is made of the removal of chloride material from alkoxysilanes.

Chung and Hayes, *J. Organometallic Chemistry,* 265(1984), pp. 135–139, discloses a process in which the chloride contamination of methoxysilanes could be significantly reduced by refluxing the methoxysilanes with metallic sodium. Chung and Hayes disclose that the problem with chloride removal is the inability to remove the alkyl chlorides. Chung and Hayes disclose the use of three separate analytical tests to determine ionic chloride, residual chloride and acidity following hydrolysis of the methoxysilane. Chung and Hayes used the residual chloride test as the criteria for measuring chloride reduction. Refluxing of crude methyltrimethoxysilane with metallic sodium was found to reduce the residual chloride content of the methyltrimethoxysilane from 400 to 5 ppm chloride. Chung and Hayes also studied refluxing methyltrimethoxysilane with other reagents and were unsuccessful in significantly reducing residual chloride content. The other reagents studied were $LiAlH_4$, tetramethylguanidine, sodium methoxide in methanol solution, potassium hydroxide in methanol solution, $(C_4H_9)SnH_2$, and magnesium oxide. The reagents studied by Chung and Hayes, with the exception of sodium metal, were ineffective in reducing the nonionic chloride level of the crude methyltrimethoxysilane. These results are summarized in Table 1 of the reference of Chung and Hayes. Thus, Chung and Hayes teach away from the disclosure of Burzynski and Martin, supra. Further, Chung and Hayes teach away from the instant invention as will be apparent from an understanding of the invention taught herein. A disadvantage of the disclosure of Chung and Hayes is the issue of safety in the handling and processing of metallic sodium on an industrial scale.

Sugihara et al., in Japanese patent application No. 255469/85, filed Nov. 14, 1985, disclose a process in which the non-hydrolyzable chloride content, from sources such as carbon-bonded chlorine, of alkoxysilanes is lowered. Sugihara et al., disclose a process in which crude alkoxysilanes are (a) treated with an acid-treated clay or metal halide at the reflux temperature of the alkoxysilane, (b) treated with a neutralizing agent, and (c) filtered or distilled to remove the solids from neutralization. Sugihara et al., disclose that their process does not achieve low residual chloride levels with treatment with a neutralizing agent without the heat treatment of the crude alkoxysilanes with an acid-treated clay or a metal halide. Sugihara et al., thus teach away from the instant invention.

The objective of the instant invention is to provide a process that will safely and effectively lower the residual chloride content of crude alkoxysilanes. A further objective of the instant invention is to provide alkoxysilanes of suitable quality for use as a chemical intermediate or for use in electronics applications.

It was found that alkaline metal oxides and hydroxides such as magnesium oxide, magnesium hydroxide, calcium oxide, calcium hydroxide, and zinc oxide are ineffective in reducing the residual chloride content of lower-boiling alkoxysilanes such as methyltrimethoxysilane when the metal oxide or hydroxide was contacted with the alkoxysilane under refluxing conditions at the atmospheric boiling point of these alkoxysilanes. However, it was unexpectedly found that by using pressure to elevate the boiling point of the lower-boiling alkoxysilane to temperatures greater than approximately 130° C. in the presence of an alkaline metal oxide or hydroxide the residual chloride content of the crude alkoxysilane could be significantly reduced. By "significantly reduced" for the purposes of this invention, we mean that the residual chlorides in the alkoxysilane can be reduced greater than one-half of their original level in the alkoxysilane. More generally, the residual chlorides can be reduced to ten percent (10%) or less of their original level in the alkoxysilane by use of this inventive method.

DESCRIPTION OF THE INVENTION

In accordance with the instant invention there is provided a process for reducing the residual chloride level of lower-boiling alkoxysilanes that will be delineated herein. What is described, therefore, is a process for reducing residual chloride level in an alkoxysilane having a boiling point at atmospheric pressure of less than about 130° C., said process comprising:

(A) contacting at a pressure greater than atmospheric and at a temperature of higher than about 130° C. the alkoxysilane and an alkaline metal compound, said compound being selected from a group consisting of (i) alkaline metal oxides and (ii) alkaline metal hydroxides;

(B) cooling the materials so contacted; and (C) separating any residual solids from the alkoxysilane, said residual solids comprising at least unreacted alkaline metal compound and salts resulting from the reaction of the alkaline metal compound and the residual chloride.

The alkoxysilanes useful in this invention are those having a boiling point at atmospheric pressure of less than 130° C. and which are selected from a group consisting of trimethoxysilane. tetramethoxysilane, dimethyldimethoxysilane, methyltrimethoxysilane, dimethyldiethoxysilane, and ethyltrimethoxysilane.

The term "residual chloride level" of alkoxysilanes as used in the instant invention is the combination of ionic and non-ionic chloride species. Ionic chloride species include free hydrogen chloride and unreacted chlorosilanes. These ionic species are readily reduced by treatment with known neutralizing agents. The non-ionic species include organic chloride materials. These organic chloride materials are believed to be impurities brought into the alkoxysilane process by the starting chlorosilane intermediates. These organic chlorides may be by-products of the alkoxysilane process. The non-ionic chloride species are ineffectively removed by a direct treatment with a single agent unless the treatment temperature is greater than about 130° C., as is disclosed in the instant invention.

The temperature needed to effect treatment of the alkoxysilane can be attained by heating the desired crude alkoxysilane in a closed system at a superatmospheric pressure. The superatmospheric pressure elevates the boiling point of the desired alkoxysilane. As an example, the boiling point of methyltrimethoxysilane at 45 psig is approximately 130° C. Crude methyltrimethoxysilane containing methanol had a boiling point range of approximately 120°-135° C. at pressures of approximately 30 to 45 psig.

The alkaline metal oxide utilized in this invention is selected from a group consisting of magnesium oxide, calcium oxide, and zinc oxide. The alkaline metal hydroxide is selected from a group consisting of magnesium hydroxide, calcium hydroxide, and zinc hydroxide. The alkaline metal oxides and hydroxides have been found to be effective in significantly reducing the residual chloride level of alkoxysilanes at a temperature of greater than about 130° C. when the alkaline metal oxide or hydroxide is present at a concentration of at least 0.25 weight percent relative to the crude alkoxysilane. The alkaline metal oxide or hydroxide may be in a form selected from a group which consists of powders, granules, pellets, beads, and lumps.

Contacting the crude alkoxysilane with an alkaline metal compound can be effected in either a batch or continuous mode. In the batch mode the crude alkoxysilane and the alkaline metal compound are added to a batch reactor, and this reaction mixture is heated under pressure to the boiling point of the alkoxysilane at the controlled superatmospheric pressure. The equipment and procedures utilized are those known in the art of design and operation of such batch equipment.

In a continuous mode, a large excess of the alkaline metal oxide or hydroxide is placed in a vessel such as a tank, column, or the like, known in the art of design of continuous reactors. The outlet of the continuous reactor is fitted with a means for maintaining a desired pressure in the reactor system. The system is brought to and maintained at the desired treatment temperature by preheating the crude alkoxysilanes, heating the vessel in which the alkaline metal compound is contained, or a combination of both. Means for preheating or heating can be effected by conventional means known in the art.

To effect significant reduction of the residual chloride level of alkoxysilanes at a temperature of greater than 130° C., the crude alkoxysilanes and an alkaline metal compound should be in contact for at least one hour.

Once the crude alkoxysilane is treated with an alkaline metal compound at a temperature greater than about 130° C., the mixture of alkoxysilane and alkaline metal compound should be cooled to facilitate safe handling. Cooling can be effected by any of many known means in the art of liquid processing.

Once the mixture of alkoxysilane and solids are cooled, the treated alkoxysilanes must be isolated from residual solids, unreacted alkaline metal compound and salts of reaction of the alkaline metal oxide and chloride impurity in the alkoxysilane, resulting from treatment. Separating solids from the treated alkoxysilane can be effected by filtration means. Filtration means can be such means as filter presses, bag filters, cartridge filters, and the like; all known techniques in the art. The treated alkoxysilane can also be removed from the solids by stripping the treated alkoxysilanes from the residual solids by heating and distilling techniques known in the art.

PREFERRED EMBODIMENT OF THE INVENTION

The preferred alkoxysilane in the instant invention is methyltrimethoxysilane.

The preferred concentration of alkaline metal compound relative to the weight of the alkoxysilane is in the range of from about 0.25 to about 1.0 weight percent.

The preferred treatment conditions are: a treatment temperature of about 150° C. or greater; a treatment pressure in the range of from about 50 psig to 100 psig; and a contact time in the range from about one to about four hours.

The preferred alkaline metal oxide is magnesium oxide.

The preferred alkaline metal hydroxide is magnesium hydroxide.

The preferred mode for contacting a crude alkoxysilane with an alkaline metal oxide is a batch mode.

The preferred means for removing residual solids from the treated alkoxysilanes is filtration.

So that those skilled in the art can better appreciate and understand the instant invention, the following examples are given. These examples are presented to be illustrative and are not to be construed as limiting the instant invention as delineated in the claims.

EXAMPLE 1

(Not within the Scope of the invention)

Methyltrimethoxysilane (MTM) with a residual chloride content of 168 parts per million (ppm), based upon the weight of the MTM, was treated with magnesium oxide (MgO) in an attempt to reduce this chloride content. The test utilized to determine the residual chloride content of the sample was carried out as follows: (1) in a polyethylene bottle, 100 grams (gm.) of MTM and 40 cubic centimeters (cc.) of warm water were shaken until the two liquid phases became compatible and heat ceased to be liberated; (2) 10 gms. of ethanol were added to assure compatibility; (3) the aqueous sample was then reacted with excess sodium methoxide to liberate free chloride ions; (4) the sample was tested by potentiometric silver nitrate titration to determine residual chloride content of the beginning MTM.

200 gms. of MTM were added to laboratory glassware suitable for heating and refluxing a liquid sample. 1.0 gm. of solid MgO was added to the MTM. The MgO was 0.5 weight percent of the total charge. The MgO loading was approximately 54 times the theoretical amount of MgO needed to react with the 168 ppm residual chloride content of the MTM.

The MTM, in the presence of the MgO, was refluxed for 2 hours at a temperature of 90° C. The sample was cooled, and the treated MTM was first filtered through filter paper to remove the MgO and other solids. The treated MTM was then filtered twice through a filter aid, to remove a haze from the liquid. The treated MTM was analyzed for residual chloride content, as described above. Final chloride content of the MTM was 144 ppm.

The above results demonstrate that treatment of methyltrimethoxysilane with magnesium oxide at a temperature of 90° C., the atmospheric boiling point, is ineffective in reducing residual chloride content.

EXAMPLE 2

MTM was treated with MgO in an attempt to reduce the residual chloride content. The MTM sample utilized was the same material as used in Example 1. Residual chloride content of the sample was 168 ppm.

The reactor utilized in the test was a laboratory reactor which was capable of being operated at elevated pressures. The reactor utilized was a Parr reactor, a laboratory apparatus known in the art of experimental reactions. Two runs were made at pressures of 75 and 97 pounds per square inch, gauge (psig), respectively, to facilitate maintaining the temperature of the MTM at approximately 150° C. Heating of the Parr reactor was effected in an air-circulating oven. In these two runs MTM and the appropriate weight of MgO to give loadings of 0.8 and 0.4 weight percent, respectively were charged to the Parr reactor. The MgO utilized was calcined magnesia, light, USP, purchased from Fischer Scientific.

The samples were held at temperature and pressure for 4 hours or more. In both runs, the treated MTM was filtered through a bed of filter aid to remove solids. A standard laboratory suction filter was utilized. Table 1 is a summary of the results of treatment observed in the two runs, designated Samples A and B, respectively.

TABLE 1

| Sample | A | B |
| --- | --- | --- |
| Weight MTM, grams | 190 | 328 |
| Weight MgO, grams | 1.5 | 1.3 |
| Weight percent MgO | 0.8 | 0.4 |
| MgO/residual chloride, mole ratio | 48 | 24 |
| Reaction time, hours | 4.0 | 4.75 |
| Pressure, psig | 75 | 97 |
| Reaction temperature, °C. | 150 | 150–157 |
| Final residual chloride, ppm | 7 | 3 |

These results demonstrate that the residual chloride content of methyltrimethoxysilane can be significantly reduced by treatment with magnesium oxide at elevated temperature and pressure.

EXAMPLE 3

Another series of runs was made to evaluate the treatment of MTM with MgO at elevated pressure and temperature. The reactor and experimental procedure were similar to those used in Example 2.

The starting MTM was analyzed to have a residual chloride content of 481 ppm. In this case the residual chloride content was analyzed by a potassium hydroxide digestion technique. In this digestion technique, 5 milliliters (ml.) of the MTM, 8 ml. ethanol, 4 potassium hydroxide pellets, and 10 drops of water were added to a pressure bomb. The bomb and its contents were heated to 120°–125° C. for 2 hours. The solution from the bomb was neutralized with 10 weight percent sulfuric acid and then potentiometrically titrated with a silver nitrate solution.

The pressure and temperature of the reactor for this series of runs was maintained at 50 psig and 150° C., respectively. The MgO loading was varied from 0 to 1.0 weight percent of the MTM. Reaction time was varied from 1 to 4 hours. Table 2 is a summary of the results of this series of runs. The individual runs are identified as Samples C, D, E, F, G, H, and I, respectively. In Table 2, the MgO loading is expressed in both weight percent of charge, designated "%", and as the multiple of the theoretical amount to react with the 481 ppm residual chloride, designated "×Excess". Reaction time is designated "Hours"; and final residual chloride content is designate "ppm Cl".

TABLE 2

| Sample | MgO Loading | | Hours | ppm Cl |
| --- | --- | --- | --- | --- |
|  | % | × Excess |  |  |
| C | 0 | — | 1 | 414 |
| D | 0.4 | 8 | 2 | 43 |
| E | 0.4 | 8 | 4 | 36 |
| F | 1.0 | 21 | 2 | 153 |
| G | 1.0 | 21 | 4 | 68 |
| H | 0.4 | 8 | 2 | 25 |
| I | 0.4 | 8 | 4 | 12 |

The results demonstrate that with as little as 8 times the theoretical excess of magnesium oxide and at reaction times as short as 2 hours, the use of pressure and temperatures significantly above the atmospheric boiling point of methyltrimethoxysilane facilitates significant reduction of the residual chloride content of methyltrimethoxysilane.

EXAMPLE 4

Two more runs were made using the same experimental procedures of Example 3. However, the MTM was analyzed for residual chloride by another technique. In this analytical technique, a sample is treated with refluxing potassium hydroxide and ethanol. After reaction, the sample is acidified with acetic acid and potentiometrically titrated with a silver nitrate solution. The starting MTM had a residual chloride content of 284 ppm.

Table 3 is a summary of the results of the two runs. The designations used in Table 3 are the same as those use in Table 2 of Example 3. The two runs are designated as Samples J and K.

TABLE 3

| Sample | MgO Loading | | Hours | ppm Cl |
| --- | --- | --- | --- | --- |
|  | % | × Excess |  |  |
| J | 0.25 | 9 | 1.5 | 33 |
| K | 0.25 | 9 | 2.5 | 13 |

The above results further demonstrate that the use of magnesium oxide at elevated temperatures and elevated pressure is effective in significantly reducing the residual chloride content of methyltrimethoxysilane.

EXAMPLE 5

A series of runs was carried out to study the effects of temperature and pressure upon the treatment of MTM with MgO to reduce the chloride content of the MTM. The reactor system and experimental procedures used were essentially the same as those used in Examples 3 and 4.

Additionally, the MTM sample was analyzed for residual chloride and ionic chloride, and by difference the non-ionic chloride which was assumed to be organic chloride. The residual chloride analysis was that used in Example 4. Ionic chloride or acidity was determined by the following procedure: (1) to 25 ml. of toluene was added 13 drops of an 0.04 weight percent methanol solution of bromocresol purple; (2) the resulting mixture was titrated to a blue-violet endpoint with 0.02 N potassium hydroxide; (3) a 10 ml. sample of the MTM was pipetted into the solution thus obtained; (4) the toluene solution of the MTM was titrated to the same blue-violet endpoint with 0.02 N potassium hydroxide. From this titration, the ionic chloride content could be calculated as ppm ionic chloride or acidity.

Using the analytical techniques described, supra, the subject sample of MTM had a residual chloride content of 178 ppm and an ionic chloride content of 25 ppm; thus an organic chloride content of 153 ppm was calculated.

Using the procedures outlined in Examples 3 and 4, pressure was varied from atmospheric pressure to over 40 psig. Temperatures were controlled at the approximate boiling point of MTM at the various pressures. The treated product was filtered in the presence of a filter aid.

Table 4 is a summary of the results of this series of runs. Four runs were made and these runs will be designated as Samples L, M, N, and 0, respectively. Pressure is designated as "psig"; temperature is designated "°C."; MgO loading, "MgO Loading". is again represented as in Examples 4 and 5. Final residual chloride and ionic chloride, expressed in ppm, as designated as "Clr" and "Cli".

TABLE 4

| Sample | MgO Loading % | × Excess | psig | °C. | Clr | Cli |
|---|---|---|---|---|---|---|
| L | 0.5 | 60 | 0 | 91 | 146 | nil |
| M | 0.25 | 30 | 16 | 105 | 149 | nil |
| N | 0.25 | 30 | 29 | 120 | 126 | nil |
| O | 0.25 | 30 | 42 | 135 | 63 | nil |

The above results demonstrate that pressure in excess of about 30 psig and temperatures in excess of 120° C. are needed to gain the benefit of significant reduction in the non-ionic or organic chloride content of methyltrimethoxysilane. These results demonstrate that ionic chloride is reduced with ease, while the reduction of non-ionic chloride is accomplished with considerable difficulty.

EXAMPLE 6

A series of runs was made to evaluate the use of other alkaline metal oxides and alkaline metal hydroxides, beyond MgO as treatment agents to reduce the residual chloride content of MTM. The treatment agents evaluated, in addition to MgO, were calcium oxide (CaO), zinc oxide (ZnO), magnesium hydroxide [Mg(OH)$_2$], and calcium hydroxide [Ca(OH)$_2$].

The experimental and analytical procedures used were similar to those utilized in Examples 2, 3, 4, and 5, supra. The starting MTM sample had a residual chloride content of 147 ppm relative to MTM. Essentially, 200 gms. of MTM and the chemical equivalent of 0.25 weight percent MgO was added to the laboratory pressure reactor. The reactor and its contents were heated and the reactor pressure was controlled so that the temperature in the reactor was maintained at 150° C. The MTM and treating agent were held at 150° C. for 4 hours. The reactor was then cooled, and the treated MTM was passed through a laboratory filter containing a diatomaceous earth filter aid.

Table 5 is a summary of the results of these evaluation runs. The runs as designated as Samples P, Q, R, S, and T, respectively. The individual treatment agents are identified, along with the weight of treatment agent added with the MTM. The results are than reported as ppm residual chloride, designated in Table 5 as "ppm Clr".

TABLE 5

| Sample | Treatment Agent | Weight gms. | Clr |
|---|---|---|---|
| P | MgO | 0.5 | 13 |
| Q | CaO | 0.7 | 8 |
| R | ZnO | 1.0 | 73 |
| S | Mg(OH)2 | 0.73 | 19 |
| T | Ca(OH)2 | 0.93 | 24 |

The above results demonstrate that alkaline metal oxides, beyond magnesium oxide, and alkaline metal hydroxides are effective in reducing the residual chloride content of methyltrimethoxysilane.

EXAMPLE 7

3585 pounds (lbs.) of crude MTM was charged to a 800-gallon agitated batch reactor. The crude MTM had a residual chloride content of 397 ppm. Chloride content was determined by the method described in Example 4. As a further test to assess the quality of the MTM, the electroconductivity of an aqueous solution of the material was checked. Using a procedure in which a 2 gm. sample of MTM is dissolved in 98 gms. of distilled water, testing of this MTM solution with an electroconductivity probe gave a result of 70 micromho/centimeter (micromho/cm.).

Approximately 16 lbs. of MgO was added with the crude MTM. This MgO loading accounted for 0.45 weight percent of the total charge or approximately 11 times the theoretical amount needed to react with the 397 ppm residual chloride.

The reactor and its contents were maintained at a pressure of between 53 and 59 psig. Once a temperature of 150° C. was reached, the reactor and its contents were held at 150° C. for six hours. The kettle contents were then cooled. A filter aid was added to the treated MTM, and this mixture was in turn passed through a plate-and-frame filter press to remove the MgO and other solids.

The final product had a residual chloride content of 60 ppm. The final product had an electroconductivity value of 7 micromho/cm. Additionally, the treated MTM was further reacted to produce a proprietary chemical material, designated in this instant invention as "Compound X", which is prone to be highly colored. Two batches of Compound X were prepared from the treated MTM. The color of the final Compound X had a Gardner color rating of 4 and 2, respectively. Historically, the color values for the Compound X ranged from 6-15.

The above results demonstrate that the quality of methyltrimethoxysilane is significantly improved by treatment with magnesium oxide at elevated pressure and temperature. In addition to significantly reducing chloride content. the product has significantly lowered electroconductivity and yields less color in a final product.

EXAMPLE 8

A laboratory-scale reactor system was operated to evaluate the continuous treatment of MTM with MgO to reduce residual chloride content. The analytical techniques utilized were similar to those in Examples 3, 4, 5, and 7, supra. The starting MTM had a residual chloride content of 465 ppm. Additionally, the starting MTM had an electroconductivity of 59 micromho/cm.

The reactor was a 1″ diameter×12″ long stainless steel column. The column was packed with MgO beads. The MgO beads had dimensions of 6 by 16 mesh. The beads were purchased from Martin Marietta under the brand name of Mag Chem 10. The reactor was packed with MgO beads so that a free volume of 72 ml. was available for liquid. MTM was continuously fed to this packed reactor with a conventional liquid feed apparatus. The reactor was equipped with a back-pressure valve so that a pressure of greater than 60 psig could be maintained in the reactor. Temperature within the reactor was maintained at 150° C. Liquid feed rates were controlled so that residence times of 40 and 90 minutes, respectively, could be evaluated.

Three separate runs were made in this continuous mode. These runs are designated as Samples U, V, and W, respectively. Table 6 is a summary of the results of these runs. The samples are identified by the residence time utilized in the run and by the resultant residual chloride and electroconductivity analyses. In Table 6, residence time in minutes is designated a "RT"; residual chloride content in ppm is designated as "Clr"; and electroconductivity in micromho/cm is designated as "EC".

TABLE 6

| Sample | RT | Clr | EC |
|--------|----|-----|-----|
| U | 40 | 59 | 6 |
| V | 40 | 138 | 11 |
| W | 90 | 48 | 4 |

These above results demonstrate that the treatment of methyltrimethoxysilane with magnesium oxide to lower total chloride content and electroconductivity can be effected in a continuous mode using elevated pressure and temperature.

What is claimed is:

1. A process for reducing residual chloride level in an alkoxysilane having a boiling point at atmospheric pressure of less than about 130° C., said process comprising:
   (A) contacting at a pressure greater than atmospheric and at a temperature of higher than about 130° C. the alkoxysilane and an alkaline metal compound, said compound being selected from a group consisting of (i) alkaline metal oxides and (ii) alkaline metal hydroxides;
   (B) cooling the materials so contacted; and
   (C) separating any residual solids from the alkoxysilane, said residual solids comprising at least unreacted alkaline metal compound and salts resulting from the reaction of the alkaline metal compound and the residual chloride.

2. A process according to claim 1, wherein the alkoxysilane is selected from a group which consists of trimethoxysilane, tetramethoxysilane, dimethyldimethoxysilane, methyltrimethoxysilane, dimethyldiethoxysilane, and ethyltrimethoxysilane.

3. A process according to claim 2, wherein the alkoxysilane is methyltrimethoxysilane.

4. A process according to claim 1, wherein contacting the alkoxysilane with an alkaline metal oxide is carried out at a temperature of about 150° C. or greater.

5. A process according to claim 1, wherein the pressure at which the alkoxysilane and the alkaline metal compound are heated in a closed system is at least 30 pounds per square inch, gauge.

6. A process according to claim 5, wherein the pressure at which the alkoxysilane and the alkaline metal oxide are heated in a closed system is in a range from about 50 to 100 pound per square inch, gauge.

7. A process according to claim 1, wherein the alkoxysilane and the alkaline metal compound are in contact for at least one hour.

8. A process according to claim 7, wherein the alkoxysilane and the alkaline metal compound are in contact in a range from about one hour to about four hours.

9. A process according to claim 1, wherein the alkaline metal oxide is selected from a group which consists of magnesium oxide, calcium oxide, and zinc oxide.

10. A process according to claim 9, wherein the alkaline metal oxide is magnesium oxide.

11. A process according to claim 1, wherein the alkaline metal hydroxide is selected from a group which consists of magnesium hydroxide, calcium hydroxide, and zinc hydroxide.

12. A process according to claim 11, wherein the alkaline metal hydroxide is magnesium hydroxide.

13. A process according to claim 1, wherein the alkaline metal compound is in a form selected from a group which consists of powders, granules, pellets, beads, and lumps.

14. A process according to claim 1, wherein the alkaline metal compound is present at a concentration of at least 0.25 weight percent relative to the alkoxysilane.

15. A process according to claim 1, wherein contacting the alkoxysilane with the alkaline metal compound is effected in a batch mode.

16. A process according to claim 15, wherein the alkaline metal compound is present at a concentration in a range of from about 0.25 to 1.0 weight percent relative to the alkoxysilane.

17. A process according to claim 1, wherein contacting the alkoxysilane with the alkaline metal compound is effected in a continuous mode.

18. A process according to claim 17, wherein the alkoxysilane is passed through a bed of solid alkaline metal compound.

19. A process according to claim 15, wherein residual solids are separated from the treated alkoxysilane by filtration.

20. A process according to claim 15, wherein residual solids are separated from the treated alkoxysilane by stripping the alkoxysilane away from residual solids.

21. A process according to claim 18, wherein residual solids leaving the bed of solid alkaline metal oxide are separated by filtration.

* * * * *